United States Patent [19]
Goldhaber

[11] Patent Number: 5,234,429
[45] Date of Patent: Aug. 10, 1993

[54] CAUTERIZATION INSTRUMENT AND ASSOCIATED SURGICAL METHOD

[76] Inventor: Neil G. Goldhaber, 201 E. 17th St., Apt. 10A, New York, N.Y. 10003

[21] Appl. No.: 908,346

[22] Filed: Jul. 6, 1992

[51] Int. Cl.$^5$ .............................................. A61B 17/36
[52] U.S. Cl. ...................................... 606/45; 606/37; 606/39; 606/49
[58] Field of Search ....................... 606/32, 37, 39, 40, 606/41, 42, 43, 44, 45, 46, 47, 48, 49, 50, 51

[56] References Cited
U.S. PATENT DOCUMENTS 5,035,695 7/1991 Weber, Jr. et al. ................... 606/42
5,098,430 3/1992 Fleenor ................................ 606/42

Primary Examiner—Stephen C. Pellegrino
Assistant Examiner—Sonya Harris
Attorney, Agent, or Firm—R. Neil Sudol; Henry D. Coleman

[57] ABSTRACT

A surgical instrument comprises a handle, an electrical cauterization electrode, a mounting for movably joining the electrode to the handle so that distance of the electrode from the handle may be adjusted prior to a surgical procedure, and an electrical supply mechanically connected to the handle and operatively connected to the electrode for supplying thereto an electrical voltage having a characteristic waveform.

7 Claims, 1 Drawing Sheet

CAUTERIZATION INSTRUMENT AND ASSOCIATED SURGICAL METHOD

BACKGROUND OF THE INVENTION

This invention relates to a cauterization instrument for use in surgery. This invention also relates to an associated surgical technique.

A Bovie pencil is a surgical cauterization instrument. An elongate electrode provided with an exposed operative tip and an electrically insulated shaft is removably joined to an elongate handle. The electrode is operatively connected via the handle to a electrical voltage source which supplies two waveforms to the handle. A switch on the handle enables a surgeon or other operator to alternately feed the different electrical waveforms to the electrode. One waveform is adapted for cauterizing organic tissue while the other is adapted for cutting.

Conventional Bovie pencils are marketed with a plurality of electrodes of different lengths. To reach a surgical site deep within a patient, such as a hernia site or up behind the diaphragm, a short electrode on the handle must be removed and replaced with a longer electrode.

Frequently, several electrode exchanges must be made during a single surgical procedure. Such electrode exchanges take time which in many cases is critical for the patient. Generally, however, electrode exchange increases the duration of surgery and raises costs.

OBJECTS OF THE INVENTION

An object of the present invention is to provide an improved Bovie type instrument.

Another object of the present invention is to provide a method for cauterization procedures in surgery.

Another, more particular, object of the present invention is to provide a Bovie type instrument wherein an adjustment in effective length may be effectuated without the necessity for electrode exchange.

A further particular object of the present invention is to provide a cauterization technique which facilitates surgery.

Yet another particular object of the present invention is to provide such a technique wherein electrode exchange is eliminated.

Other objects of the present invention will be apparent from the detailed descriptions and drawings included herein.

SUMMARY OF THE INVENTION

A surgical instrument comprises, in accordance with the present invention, a handle, an electrical cauterization electrode, a mounting for movably joining the electrode to the handle so that distance of the electrode from the handle may be adjusted prior to a surgical procedure, and an electrical supply mechanically connected to the handle and operatively connected to the electrode for supplying thereto an electrical voltage having a characteristic waveform.

A surgical instrument comprises, in accordance with a more particular characterization of the present invention, a handle, an electrical cauterization electrode slidably mounted to the handle so that distance of the electrode from the handle may be adjusted prior to a surgical procedure, and an electrical supply mechanically connected to the handle and operatively connected to the electrode for supplying thereto an electrical voltage having a characteristic waveform.

Pursuant to another feature of the present invention, the electrode takes the form of a telescoping rod having a plurality of segments slidably mounted with respect to each other and with respect to the handle.

A method for use in performing a surgical operation comprises, in accordance with the present invention, the steps of (a) providing an electrical cauterization instrument having a handle and a cauterization electrode mounted to the handle, (b) moving the electrode relative to the handle to adjust the distance of an operative tip of the electrode from the handle, (c) engaging organic tissues with the operative tip, and (d) during the step of engaging, supplying to the electrode an electrical voltage having a characteristic waveform, thereby effectuating a cauterization of the organic tissues engaged by the operative tip.

Pursuant to another feature of the present invention, the method further comprises the step of (e) inserting the electrode through a small opening in a patient, the organic tissues being located inside the patient, (f) removing the electrode from the patient, (g) again moving the electrode relative to the handle to readjust the distance of the operative tip from the handle, (h) again inserting the electrode through a small opening in a patient, (i) subsequently engaging different organic tissues with the operative tip, and (j) during the step of subsequently engaging, supplying electrical current to the electrode.

Where the electrode takes the form of a telescoping rod, the step of moving includes the step of at least partially collapsing the rod or partially extending the rod.

An improved Bovie type instrument in accordance with the present invention facilitates cauterization procedures in surgery. The number of spare instrument parts which must be handled and accounted for is reduced. As a general proposition, surgical time is reduced. Adjustment in effective length of the Bovie may be effectuated without the necessity for electrode exchange.

DETAILED DESCRIPTION

Figure 1:
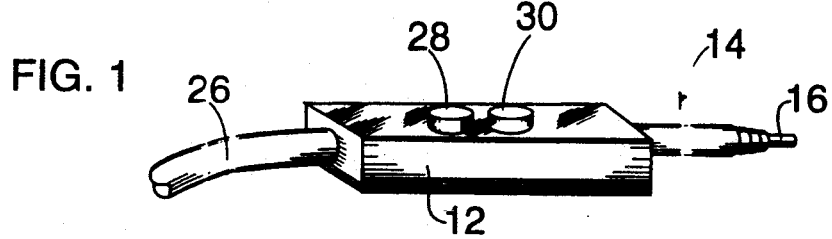
FIG. 1 is a schematic side perspective view of a Bovie type cauterization instrument in accordance with the present invention, showing a cauterization electrode in a retracted configuration.
Figure 2:
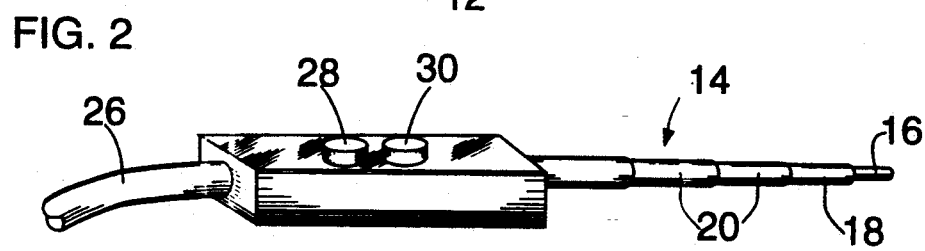
FIG. 2 is a schematic side perspective view of the Bovie type cauterization instrument of FIG. 1, showing the cauterization electrode in an extended configuration.

As illustrated in FIGS. 1 and 2, a Bovie type cauterization instrument for use in surgery comprises an elongate handle 12, and an electrical cauterization electrode 14 slidably mounted to handle 12 so that distance of an operative tip 16 of the electrode from handle 12 is adjustable.

Figure 3:
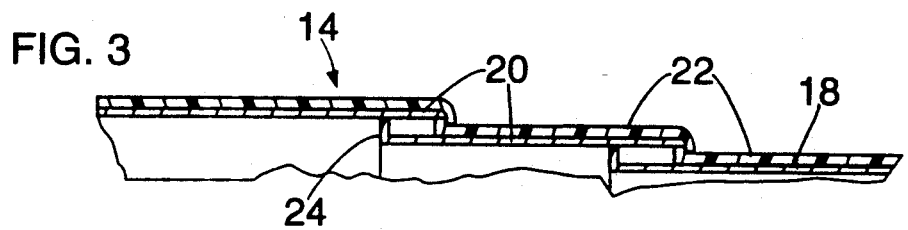
FIG. 3 is a partial longitudinal cross-sectional view, on an enlarged scale, of the electrode illustrated in FIG. 2.

Specifically, as illustrated in FIG. 3, electrode 14 takes the form of an outermost tube 18 in a series of telescoping tubes 20. Operative tip 16 is connected to tube 18 for electrical conduction.

Tubes 20, including tube 18, are provided along outer surfaces with respective layers 22 of electrically insulating material such as rubber or polyethylene. Tubes 20, including tube 18, are connected to one another via electrically conductive contacts 24 in the form of outwardly projecting flanges.

The instrument of FIGS. 1 and 2 further comprises an electrical supply line 26 mechanically connected to handle 12 and operatively connected to electrode 14 for supplying thereto an electrical voltage having a characteristic waveform. More specifically, as in conventional Bovie type surgical instruments, line 26 carries a pair of voltages each having a characteristic waveform for implementing cauterization and cutting operations, respectively. A surgeon or other operator selects between the two voltages by pressing respective push buttons 28 and 30 on handle 12. Push buttons 28 and 30 may alternatively take the form of a toggle switch (not shown) or other equivalent actuator.

In using the instrument of FIGS. 1-3, telescoping tubes 20 are pulled out from the retracted configuration of FIG. 1 to the extended rod-like configuration of FIG. 2 (or a configuration of intermediate length, not shown) in order to enable the surgeon to reach a surgical site located relatively deep inside a patient. The extended rod-like configuration of electrode 14 may be used during laparoscopic surgery to insert operative cauterization tip 16 through a trocar sleeve or laparoscopic cannula (not shown) into the patient's abdomen.

After cauterization of a surgical site, the patient may require cutting or cauterization at a different location which is closer or farther from the opening through which the surgeon is working. In that event, electrode 14 is withdrawn from the patient and tubes 20 are slid with respect to one another and to handle 12 so that the length of electrode 14 more closely matches the distance of the new surgical site from the access opening. Electrode 14 is then reinserted into the patient, the operative tip 16 is brought into contact with organic tissue, and button 28 or 30 is pressed to effectuate an electrical cauterization or cutting operation.

Figure 4:
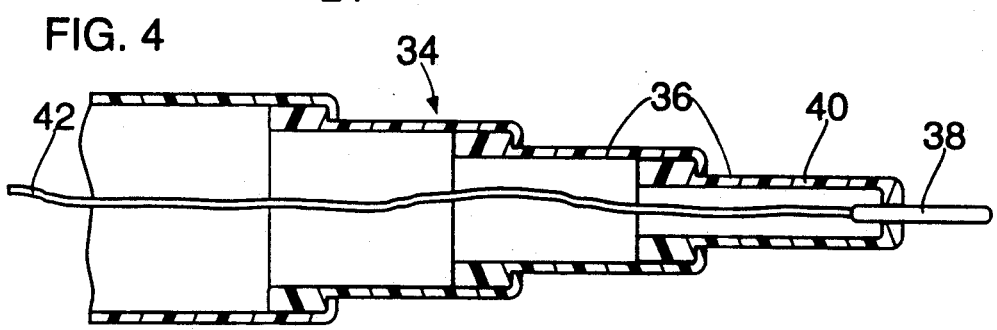
FIG. 4 is a partial longitudinal cross-sectional view, on an even larger scale, of another electrode utilizable in the Bovie type instrument of FIGS. 1 and 2.

As illustrated in FIG. 4, a telescoping member 34 for a Bovie type cauterization instrument comprises a plurality of interfitting tubular members 36 made of an electrically nonconductive polymeric material. An electrode 38 is embedded in the distal end of a tubular member 40 at the free end of telescoping member 34. Electrode 38 is connected to a flexible (collapsible) wire 42 in turn connected to a source of electrical voltage via handle 12 (FIGS. 1 and 2) and buttons 28 and 30.

Figure 5:
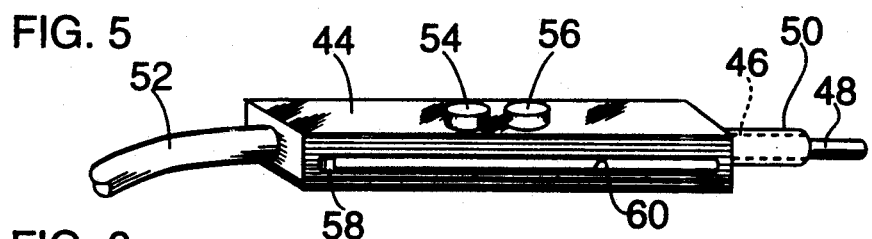
FIG. 5 is a schematic side perspective view of another Bovie type cauterization instrument in accordance with the present invention, showing a cauterization electrode in a retracted configuration.
Figure 6:
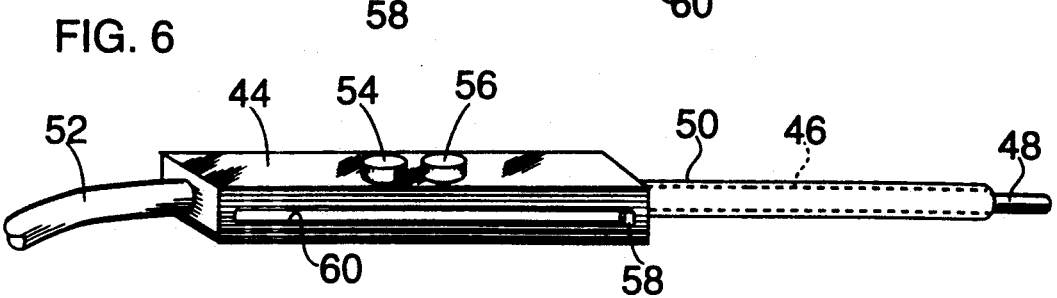
FIG. 6 is a schematic side perspective view of the Bovie type cauterization instrument of FIG. 5, showing the cauterization electrode in an extended configuration.

As depicted in FIGS. 5 and 6, another Bovie type instrument comprises an elongate handle 44, and an electrical cauterization electrode 46 in the form of a rigid rod slidably mounted to handle 44 so that distance of an operative tip 48 of the electrode from handle 44 is adjustable.

Electrode rod 46 is provided essentially along its length with a layer 50 of electrically insulating material such as rubber or polyethylene.

The instrument of FIGS. 5 and 6 further comprises an electrical supply line 52 mechanically connected to handle 44 and operatively connected to electrode rod 46 for supplying thereto an electrical voltage having a characteristic waveform. The connection of line 52 to electrode rod 46 may be implemented inside handle 44 by a contact ring or a brush type contact (not shown) which slides along an elongate conductor (not shown).

As discussed hereinabove with reference to FIGS. 1 and 2, line 52 carries a pair of voltages each having a characteristic waveform for implementing cauterization and cutting operations, respectively. A surgeon or other operator selects between the two voltages by pressing respective push buttons 54 and 56 on handle 44. Push buttons 54 and 56 may alternatively take the form of a toggle switch (not shown) or other equivalent actuator.

Electrode rod 46 is provided at a proximal end with a manual actuator knob 58 which extends through a slot 60 in handle 44. In using the instrument of FIGS. 5 and 6, electrode rod 46 is pushed from the retracted or shortened configuration of FIG. 5 to the extended configuration of FIG. 6 by pushing actuator knob 58 with a thumb or finger. Retraction of electrode rod 46 is accomplished in the same way.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. A surgical instrument comprising:
    a handle;
    an electrical cauterization electrode movably mounted to said handle so that distance of said electrode from said handle may be adjusted prior to a surgical procedure, said electrode taking the form of a telescoping rod having a plurality of segments slidably mounted with respect to each other and with respect to said handle; and
    electrical supply means mechanically connected to said handle and operatively connected to said electrode for supplying thereto an electrical voltage having a characteristic waveform.

2. A method for use in performing a surgical operation, comprising the steps of:
    providing an electrical cauterization instrument having a handle and a cauterization electrode mounted to said handle, said electrode taking the form of a telescoping rod;
    moving said electrode relative to said handle to adjust the distance of an operative tip of said electrode from said handle, said step of moving including the step of at least partially collapsing said rod;
    engaging organic tissues with said operative tip; and
    during said step of engaging, supplying to said electrode an electrical voltage having a characteristic waveform, thereby effectuating a cauterization of the organic tissues engaged by said operative tip.

3. The method defined in claim 2, further comprising the step of inserting said electrode through a small opening in a patient, said organic tissues being located inside the patient.

4. The method defined in claim 3, further comprising the steps of removing said electrode from the patient, again moving said electrode relative to said handle to readjust the distance of said operative tip from said handle, again inserting said electrode through a small opening in a patient, subsequently engaging different organic tissues with said operative tip, and during said step of subsequently engaging, supplying electrical current to said electrode.

5. A method for use in performing a surgical operation, comprising the steps of:
 providing an electrical cauterization instrument having a handle and a cauterization electrode mounted to said handle, said electrode taking the form of a telescoping rod;
 moving said electrode relative to said handle to adjust the distance of an operative tip of said electrode from said handle, said step of moving including the step of at least partially extending said rod;
 engaging organic tissues with said operative tip; and
 during said step of engaging, supplying to said electrode an electrical voltage having a characteristic waveform, thereby effectuating a cauterization of the organic tissues engaged by said operative tip.

6. The method defined in claim 5, further comprising the step of inserting said electrode through a small opening in a patient, said organic tissues being located inside the patient.

7. The method defined in claim 6, further comprising the steps of removing said electrode from the patient, again moving said electrode relative to said handle to readjust the distance of said operative tip from said handle, again inserting said electrode through a small opening in a patient, subsequently engaging different organic tissues with said operative tip, and during said step of subsequently engaging, supplying electrical current to said electrode.

* * * * *